United States Patent
Paulin et al.

(10) Patent No.: US 11,380,215 B2
(45) Date of Patent: Jul. 5, 2022

(54) REWARD-BASED ECOSYSTEM FOR TRACKING NUTRITIONAL CONSUMPTION

(71) Applicant: KYNDRYL, INC., New York, NY (US)

(72) Inventors: Paulo Henrique Paulin, Florianopolis (BR); Carlos Demetrio de Souza, Campinas (BR); Marco Aurelio Stelmar Netto, Sao Paulo (BR); Cesar Penna Santana, Campinas (BR)

(73) Assignee: KYNDRYL, INC., New York, NY (US)

( * ) Notice: Subject to any disclaimer, the term of this patent is extended or adjusted under 35 U.S.C. 154(b) by 652 days.

(21) Appl. No.: 16/118,387

(22) Filed: Aug. 30, 2018

(65) Prior Publication Data

US 2020/0074882 A1 Mar. 5, 2020

(51) Int. Cl.
G09B 19/00 (2006.01)
G16H 20/60 (2018.01)

(52) U.S. Cl.
CPC ......... *G09B 19/0092* (2013.01); *G16H 20/60* (2018.01)

(58) Field of Classification Search
CPC .............................. G09B 19/0092; G09B 23/28
(Continued)

(56) References Cited

U.S. PATENT DOCUMENTS 7,999,674 B2 * 8/2011 Kamen ................ A61B 5/0002 340/572.1
8,506,396 B1 * 8/2013 Snyder ................... G16H 20/30 463/31
(Continued)

FOREIGN PATENT DOCUMENTS

CN 104841126 A 8/2015
IN 201741032570 A 10/2017
(Continued)

OTHER PUBLICATIONS

Bogden, "Technology and Nutrition: Interactive Strategies for Children to Learn Nutrition," Western Michigan University Honors Theses, Apr. 22, 2015, p. 1-55, Paper 2601.
(Continued)

*Primary Examiner* — Kurt Fernstrom
(74) *Attorney, Agent, or Firm* — Erik Swanson; Andrew M. Calderon; Roberts Calderon Safran & Cole, P.C.

(57) ABSTRACT

A method, computer system, and a computer program product for tracking a nutritional consumption is provided. The present invention may include providing a digital entity associated with a participant. The present invention may also include transmitting a dietary goal to a device associated with the digital entity, including a nutritional requirement for the participant. The present invention may include recognizing at least one food item consumed by the participant. The present invention may also include determining a consumed nutrient information associated with the recognized at least one food item consumed by the participant. The present invention may also include, in response to determining that the nutritional requirement of the transmitted dietary goal is met by the determined consumed nutrient information, releasing a reward to the device associated with the digital entity, wherein the released reward is associated with an accomplishment of the dietary goal by the participant.

20 Claims, 7 Drawing Sheets

(58) Field of Classification Search
USPC .......................................................... 434/127
See application file for complete search history.

(56) References Cited

U.S. PATENT DOCUMENTS

| | | | |
|---|---|---|---|
| 8,690,578 B1* | 4/2014 | Nusbaum | G09B 19/00 434/127 |
| 9,011,153 B2* | 4/2015 | Bennett | G16H 20/30 434/127 |
| 9,254,099 B2 | 2/2016 | Connor | |
| 10,702,773 B2* | 7/2020 | Davis | G06N 3/006 |
| 10,967,261 B2* | 4/2021 | Morrison | A63F 13/35 |
| 2003/0091964 A1* | 5/2003 | Yeager | G16H 20/60 434/127 |
| 2009/0275002 A1* | 11/2009 | Hoggle | G09B 19/0092 434/127 |
| 2009/0300525 A1* | 12/2009 | Jolliff | H04M 1/72451 715/764 |
| 2010/0310725 A1 | 12/2010 | Reidy et al. | |
| 2012/0254196 A1 | 10/2012 | Abramski et al. | |
| 2013/0295530 A1 | 11/2013 | Townsend et al. | |
| 2014/0240339 A1* | 8/2014 | Hsiao | G06T 11/00 345/589 |
| 2014/0349256 A1 | 11/2014 | Connor | |
| 2015/0093725 A1* | 4/2015 | Baarman | G16H 20/60 434/127 |
| 2015/0118659 A1* | 4/2015 | Meyer | G16H 20/60 434/127 |
| 2015/0140523 A1* | 5/2015 | Dewan | G09B 19/0092 434/127 |
| 2015/0168365 A1 | 6/2015 | Connor | |
| 2015/0262507 A1 | 9/2015 | Hanlon et al. | |
| 2015/0294593 A1* | 10/2015 | Schoen | G16H 20/60 434/127 |
| 2015/0294594 A1* | 10/2015 | Pacione | A61B 5/053 434/127 |
| 2015/0371553 A1* | 12/2015 | Vento | G16H 20/60 434/127 |
| 2015/0371554 A1 | 12/2015 | Garber | |
| 2016/0035248 A1* | 2/2016 | Gibbs | G09B 5/02 434/127 |
| 2016/0042660 A1* | 2/2016 | Radovcic | G16H 20/60 434/127 |
| 2016/0063888 A1* | 3/2016 | McCallum | A63B 24/0075 434/127 |
| 2016/0071423 A1* | 3/2016 | Sales | A61B 5/4076 434/127 |
| 2016/0071432 A1* | 3/2016 | Kurowski | G16H 20/10 434/127 |
| 2016/0129350 A1* | 5/2016 | Khalsa | H04N 21/44222 463/31 |
| 2016/0140869 A1* | 5/2016 | Kuwahara | G16H 20/60 434/127 |
| 2016/0155356 A1 | 6/2016 | Heyer et al. | |
| 2016/0166195 A1* | 6/2016 | Radecka | A61B 5/7475 434/127 |
| 2016/0228745 A1* | 8/2016 | Rous | G16H 20/30 |
| 2016/0253922 A1* | 9/2016 | Kremen | G09B 19/0092 434/127 |
| 2016/0379520 A1* | 12/2016 | Borel | G09B 19/0092 434/127 |
| 2017/0080346 A1* | 3/2017 | Abbas | A63F 13/79 |
| 2017/0220772 A1 | 8/2017 | Vleugels et al. | |
| 2018/0358129 A1* | 12/2018 | Gorzelniak | G16H 50/50 |
| 2019/0070507 A1* | 3/2019 | Van Deren | A63F 13/69 |
| 2019/0163270 A1* | 5/2019 | Da Silva | G06F 1/163 |
| 2019/0252058 A1* | 8/2019 | Wolf | G16H 20/60 |

FOREIGN PATENT DOCUMENTS

| | | |
|---|---|---|
| WO | 2017123175 A1 | 7/2017 |
| WO | 2017132690 A1 | 8/2017 |

OTHER PUBLICATIONS

Gillis, "Use of an Interactive Game to Increase Food Acceptance—A Pilot Study," Child: Care, Health and Development, Sep. 2003, p. 1, vol. 29, Issue 5, Abstract Only, https://onlinelibrary.wiley.com/doi/pdf/10.1046/j.1365-2214.2003.00354.x, Accessed on Aug. 24, 2018.

Mell et al., "The NIST Definition of Cloud Computing," National Institute of Standards and Technology, Sep. 2011, p. 1-3, Special Publication 800-145.

* cited by examiner

REWARD-BASED ECOSYSTEM FOR TRACKING NUTRITIONAL CONSUMPTION

BACKGROUND

The present invention relates generally to the field of computing, and more particularly to health and nutrition.

Health problems stemming from improper food consumption are widely known issues impacting both adults and young children. Young children may be particularly susceptible to eating disorders, such as Avoidant Restrictive Food Intake Disorder (ARFID), a newly introduced diagnosis in the Diagnostic and Statistical Manual of Mental Disorder, Fifth Edition (DSM-5), caused by difficulties eating with others and extended times needed to eat. In addition to nutritional health concerns, ARFID may lead to children developing socialization problems in schools and other communal environments. Accordingly, it may be beneficial to provide children with proper nutrition-related education to instill healthy food habits from a young age.

SUMMARY

Embodiments of the present invention disclose a method, computer system, and a computer program product for tracking a nutritional consumption. The present invention may include providing a digital entity associated with a participant. The present invention may also include transmitting a dietary goal to a device associated with the digital entity, including a nutritional requirement for the participant. The present invention may include recognizing at least one food item consumed by the participant. The present invention may also include determining a consumed nutrient information associated with the recognized at least one food item consumed by the participant. The present invention may also include, in response to determining that the nutritional requirement of the transmitted dietary goal is met by the determined consumed nutrient information, releasing a reward to the device associated with the digital entity, wherein the released reward is associated with an accomplishment of the dietary goal by the participant.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
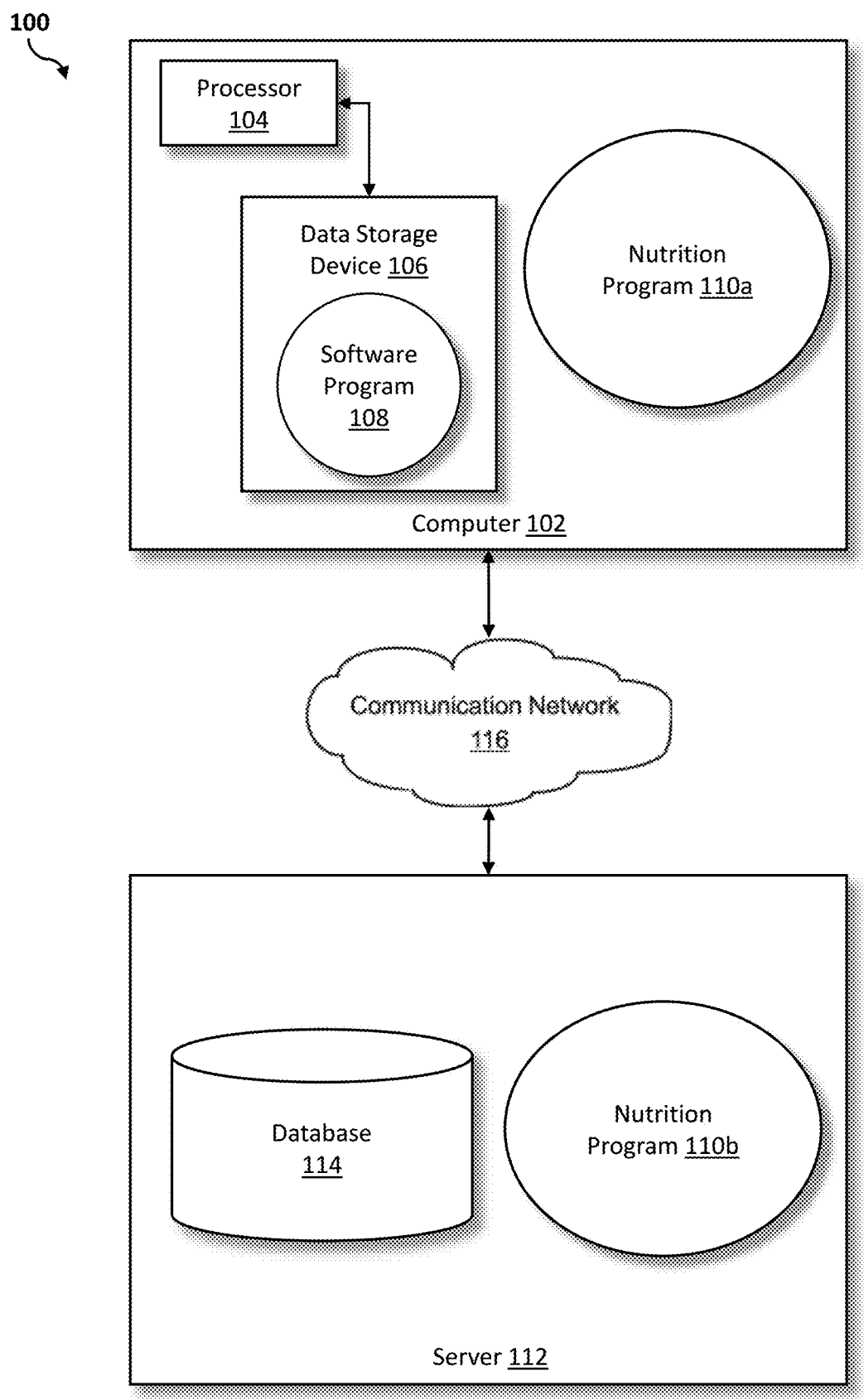
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for tracking the nutritional consumption of a participant using reward-based dietary goals. As such, the present embodiment has the capacity to improve the technical field of health and nutrition by engaging a participant user (e.g., a child) to follow the requirements of a dietary goal in exchange for a reward and other positive feedback. More specifically, a stakeholder user (e.g., a parent, doctor, teacher, or other third-party) associated with the participant may set a dietary goal for the participant. Then, the participant may receive the instructions to follow the dietary goal by engaging with a digital entity in a gamified interface. The digital entity may also notify the participant regarding the possible rewards and incentives for accomplishing the dietary goal. The reward for accomplishing the dietary goal may include enhancements for the digital entity, such as badges, ornaments, ribbons, and other accessories indicating the dietary goal accomplishments of the participant. The participant may share the status of the dietary goals and accomplishments through a social media network. However, if the dietary goal is not accomplished by the participant, alternative recommendations may be provided to any stakeholder (e.g., parent, teacher, doctor) to achieve the objective of the dietary goal and facilitate compliance of the dietary goal by the participant.

As described previously, health problems stemming from improper food consumption are widely known issues impacting both adults and young children. Young children may be particularly susceptible to eating disorders such as Avoidant Restrictive Food Intake Disorder (ARFID), a newly introduced diagnosis in the Diagnostic and Statistical Manual of Mental Disorder, Fifth Edition (DSM-5), caused by difficulties eating with others and extended times needed to eat. In addition to nutritional health concerns, ARFID may lead to children developing socialization problems in schools and other communal environments. Accordingly, it may be beneficial to provide children with proper nutrition-related education to instill healthy food habits from a young age.

Therefore, it may be advantageous to, among other things, provide an ecosystem for engaging a participant to follow one or more prescribed dietary goals in exchange for rewards, incentives, recognition, and other positive feedback. A reward-based ecosystem may provide the participant with the dietary goal through a gamified interface, may track the nutritional consumption of the participant to determine the dietary goal status, and may reward the participant for the dietary goal accomplishments. It may be advantageous to provide a cognitive component which may leverage artificial intelligence capabilities, machine learning capabilities, and visual recognition capabilities to identify the foods and drinks consumed by the participant and provide recommendations for food preparation and replacement ingredient techniques to track and improve the dietary habits of the participant. It may be further advantageous to provide a social sharing component which may incentivize the participant to establish healthy nutritional habits through positive social recognition.

According to at least one embodiment, the stakeholder user may include a moderator, such as, the parent of the child. A dietary goal may be created or accepted by the parent. The parent may access a dashboard of the system with an associated user identification ("ID") and password. The parent may access (e.g., via the dashboard) one or more automatic dietary goal recommendations determined by the system based on the health information and the nutritional history of the child. For example, the system may recommend reducing sugar ingestion, eating specific vegetables, avoiding high caloric candies, taking meals before certain times, or generally eating healthy. The parent may accept the automatic dietary goal recommendation or may create a custom dietary goal.

According to at least one embodiment, the stakeholder user may include a contributor, such as a doctor, a teacher, or a third-party service associated with the child. In one embodiment, the contributor may submit a dietary goal recommendation. The doctor and the teacher may access the dashboard of the system with a respective user ID and password. The doctor may create specific dietary goal recommendations for the child related to health treatments or related to preventative measures. The teacher may create specific dietary goal recommendations for the child related to nutrition education lessons, awareness projects, and other school efforts. The third-party service (e.g., toy store, social/religious organization, civil association) may create dietary goal recommendations for the child related to nutritional awareness campaigns. The parent may access the dashboard with the associated user ID and password to accept/approve any of the dietary goal recommendations submitted by the doctor, teacher, or third-party service.

According to at least one embodiment, the child, the parent, or a caregiver of the child may receive and share goals, recommendations, accomplishments, and awards via a social media network. In one embodiment, the social media network may be provided to improve the speed in which doctors, clinics, and third-party services may communicate with parents/caregivers and children to deliver society-wide nutrition education and establish healthy food habits. In another embodiment, communications to/from doctors, clinics, and third-party services (including goals, recommendations, and progression) may be transmitted through a private communication channel. The social interaction over a computer network may be made public after approval from a guardian (e.g., the parent/caregiver) of the child. The guardian may determine the audience that may access the sensitive information associated with the child and the circumstances under which the sensitive information may be shared. Dietary goals for the child may be created/assigned by the guardians, health care professionals (e.g., doctors, clinics, health insurers), teachers, and other third-party services via the social media network. The dietary goals may be unique to a single child, catered to a specific group of children (e.g., school, class, family), and/or open to any child (e.g., contest created by a third-party service). Specific dietary goal status updates (e.g., goal accomplishments) may be shared upon authorization (e.g., by the guardian) with the goal creators, stakeholders, and other authorized users via the social media network. In another embodiment, the specific dietary goal status updates may be shared with the goal creators, stakeholders, and other authorized users through a private communication channel. The dietary goal status updates may be individual-based or group-based depending on the goal type (e.g., individual participant or group of participants). In one embodiment, the dietary goal status may be used to update the medical record of the participant. In one embodiment, the dietary goal status may be used to collect research data associated with the food ingestion habits of a population. In another embodiment, the dietary goal status may be used to define the winners of a dietary goal contest provided by a third-party service. The winners may be given the right (e.g., reward voucher) to redeem discounts, gifts, amenities, or other material goods. In at least one embodiment, the dietary goal status may be used to provide a teacher or a school with feedback on a food ingestion education program. In another embodiment, the dietary goal status may include other suitable uses (e.g., nutritional health study of a population).

According to one embodiment, a cognitive component including artificial intelligence and machine learning may be provided to track and assist the nutritional consumption of the participant. The system may collect feedback from the subject matter experts (SMEs), including the stakeholders (e.g., parents, doctors, teachers, third-party services) and participants (e.g., children), and may generate a training data corpus from the collected feedback. In one embodiment, the children may use the gamified interface to provide a grading value (e.g., via like/dislike) of the earned badges and/or evolution steps of the digital entity. In another embodiment, the children may use the gamified interface to provide a grading value (e.g., via like/dislike) of the food recommendation through the digital entity. In one embodiment, the parent/caregiver may provide feedback (e.g., via the dashboard) about the earned badges and/or evolution steps of the digital entity. In one embodiment, the parent/caregiver may use the dashboard to provide feedback on the recommended ingredients, cooking techniques, and enjoyment of the food by the child. In one embodiment, the doctor may use the dashboard to provide feedback on the health condition of the child in terms of the created dietary goals. In one embodiment, the school teachers/coordinators may use the dashboard to provide feedback on the community acceptance and participation in a certain dietary goal. In one embodiment, third-party service providers may provide feedback on the community participation in the third-party created dietary goals. The cognitive component may access the training data corpus to learn from the feedback of the SMEs.

According to one embodiment, after the training/learning period of the cognitive component, the trained system may provide more engaging badges/evolutionary steps for the digital entity to increase enthusiasm and participation by the children. In another embodiment, the trained system may provide more enjoyable healthy food recommendations for the children. In another embodiment, the trained system may provide simpler meal preparation recommendations for the parent/caregiver in order to increase participation by the parent/caregiver. In another embodiment, the trained system may provide doctors with better health treatment-related dietary goal recommendations to increase the health treatment success rate in the children. In at least one embodiment, the trained system may provide third-party services with more engaging nutritional campaigns to increase participation.

According to one embodiment, the digital entity may serve as the main interface with the child. The digital entity may include a virtual avatar selected and personalized by the child or the parent/caregiver. The virtual avatar may include a representation of an animal, a flower, a toy, a game/cartoon character, an emoji, or any animated character. The virtual avatar may interact with the child through textual, visual, and audio feedback. The interactions between the virtual avatar and the child may vary based on the age, gender, cultural characteristics (e.g., country, language, religion/belief), and social/developmental characteristics (e.g., Autism, Asperger's Syndrome) of the child. Through the interactions between the virtual avatar and the child, the digital entity may provide the food ingestion recommendations directly associated with the dietary goals created or approved by the parent/caregiver and may depict the virtual evolution of the digital entity (e.g., increase in size, strength, format, color, health).

According to at least one embodiment, the digital entity may evolve according to the dietary goal accomplishments of the child. The dietary goals may include eating vegetables/fruits daily during a period of time, increasing/reducing food consumption, limiting fast food consumption to once a month, eating a different food type, and eating a new vegetable/fruit. In one embodiment, the age of the child may impact the frequency of the digital entity evolution. For example, the digital entity of a toddler may depict minor evolutions after every meal since younger children may not understand long term objectives. For older children who may understand long term objectives, the digital entity may provide compliments for short-term accomplishments. Additionally, the digital entity may depict weekly mid-term evolutions accompanied with monthly, major evolutions. In another embodiment, the digital entity evolution may vary based on the specific or collective dietary goal of the participant.

According to another embodiment, a reward system may be provided through which the stakeholders (e.g., moderators, contributors) may define the evolutionary steps of the digital entity based on one or more system recommended parameters (e.g., according to the age of the child). For example, a third-party service may offer a customized evolutionary reward for a collective goal, such as a badge or an accessory, which the parent/caregiver or the child (upon parent/caregiver approval) may share on the social media network. The reward system may highlight the accomplishments of a participant within a participant group in order to incentivize the participant group to engage in the collective goal. It is contemplated that dietary goal accomplishments may be depicted through the evolutionary steps of the digital entity as well as through the badges earned by the digital entity.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a nutrition program 110a. The networked computer environment 100 may also include a server 112 that is enabled to run a nutrition program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 5, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the nutrition program 110a, 110b may interact with a database 114 that may be embedded in various storage devices, such as, but not limited to a computer/mobile device 102, a networked server 112, or a cloud storage service.

According to the present embodiment, a moderator (e.g., a parent) using a client computer 102 or a server computer 112 may use the nutrition program 110a, 110b (respectively) to transmit a dietary goal to a participant (e.g., a child). The nutrition program 110a, 110b may record the status of the dietary goal and, in response to determining that the dietary goal is accomplished by the participant, the nutrition program 110a, 110b may release a predetermined reward to participant. The reward-based nutrition method is explained in more detail below with respect to FIGS. 2-4.

Figure 2:
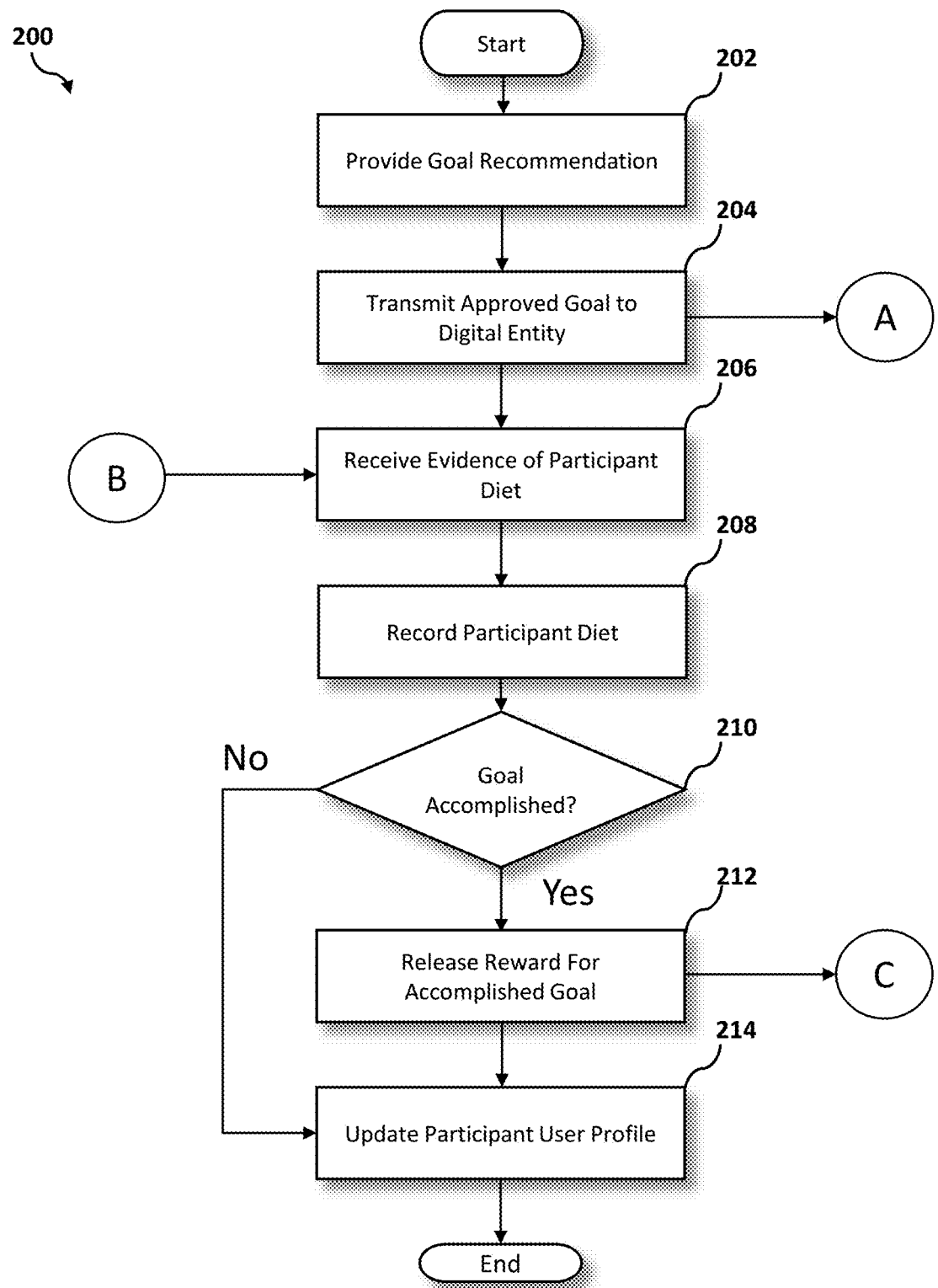
FIG. 2 is an operational flowchart illustrating a reward-based nutrition process according to at least one embodiment.

Referring now to FIG. 2, an operational flowchart illustrating the exemplary reward-based nutrition process 200 used by the nutrition program 110a, 110b according to at least one embodiment is depicted.

At 202 a goal recommendation is provided. The nutrition program 110a, 110b may provide a moderator (e.g., a parent) with one or more dietary goal recommendations for a participant (e.g., a child) associated with the moderator. In one embodiment, the nutrition program 110a, 110b may receive the dietary goal recommendations from various entry points or contributors (e.g., doctors, teachers, third-party entities) associated with the participant. The nutrition program 110a, 110b may provide the moderator with the option to accept/approve one or more of the dietary goal recommendations received from the various contributors. The nutrition program 110a, 110b may also provide the moderator with the option to create one or more dietary goals for the participant.

According to one embodiment, the moderator may run the nutrition program 110a, 110b on a moderator device (e.g., client computer 102). The nutrition program 110a, 110b may provide a moderator dashboard which the moderator may access to accept/approve the dietary goal recommendation received from the contributor and/or create the dietary goal for the participant.

Before providing the moderator with access to the moderator dashboard, the nutrition program 110a, 110b may prompt the moderator (e.g., via a dialog box in a sign in page) to log in to a moderator profile associated with the moderator or initialize a new moderator profile if the moderator is not a return user. In one embodiment, the moderator may textually enter an identifier (e.g., username, e-mail address) and a password to log in to the moderator profile. For a new moderator, the nutrition program 110a, 110b may initialize the new moderator profile using one or more known methods and may upload the initialized moderator profile to a cloud environment for storage on the server 112 via a communication network 116. On the server 112, the initialized moderator profile may be stored within an account repository, for example, in a database 114.

The nutrition program 110a, 110b may also provide a participant user profile for each participant (e.g., child) in the reward-based nutrition process 200. In one embodiment, the nutrition program 110a, 110b may provide the moderator with the option (e.g., via the moderator dashboard) to link the moderator profile with the participant user profile of the participant associated with the moderator. By linking the moderator profile with the participant user profile, the nutrition program 110a, 110b may provide the moderator with administrative privileges over the participant user profile. As such, the moderator may administer, monitor, and update the dietary goals of the participant via the moderator dashboard.

The nutrition program 110a, 110b may provide the moderator with the option to initialize a new participant user profile (e.g., via the moderator dashboard) if the participant associated with the moderator is not a return user. When initializing the new participant user profile, the nutrition program 110a, 110b may provide the moderator with one or more text fields for entering the participant data. The moderator may textually enter participant identifying information such as the name, username, and e-mail address of the participant. In one embodiment, the moderator may textually enter additional participant data including, gender, height, weight, food preferences, food allergies/intolerances, health conditions, chronic diseases, eating disorders, eating/food restrictions (e.g., gluten-free, religion-related, lactose intolerant, vegetarian, vegan, diabetic, macrobiotic), and other participant data pertinent to the nutritional history of the participant. In one embodiment, the nutrition program 110a, 110b may provide the moderator with the option to select one or more privacy preferences for the initialized participant user profile (e.g., public profile or private profile). The nutrition program 110a, 110b may initialize the new participant user profile using one or more known methods and may upload the initialized participant user profile to a cloud environment for storage on the server 112 via a communication network 116. On the server 112, the initialized participant user profile may be stored within an account repository, for example, in a database 114.

According to one embodiment, one or more contributors (e.g., doctor, teacher, third-party service) in the reward-based nutrition process 200 may run the nutrition program 110a, 110b on a respective contributor device (e.g., client computer 102). The nutrition program 110a, 110b may provide a contributor dashboard which the contributor may access to submit one or more dietary goal recommendations for the participant. Before providing the contributor with access to the contributor dashboard, the nutrition program 110a, 110b may prompt the contributor (e.g., via a dialog box in a sign in page) to log in to a contributor user profile associated with the contributor or initialize a new contributor user profile if the contributor is not a return user.

After the contributor is logged in to the contributor user profile, the nutrition program 110a, 110b may direct the contributor to the contributor dashboard where the contributor may find and select one or more intended participants for the dietary goal recommendation. The nutrition program 110a, 110b may provide a search field in the contributor dashboard in which the contributor may textually enter a participant identifier (e.g., name, username, e-mail address). The contributor may then select the intended participant from the result of the participant search. In one embodiment, the nutrition program 110a, 110b may enable the contributor to find and select an intended participant group (e.g., all 5 to 7-year-old participants; all kindergarten students at a school). To that end, the nutrition program 110a, 110b may provide an advanced search mechanism in the contributor dashboard to enable the contributor to search for intended participants based on participant demographics (e.g., gender, age) or other participant characteristics (e.g., school).

After receiving the intended participant selection from the contributor, the nutrition program 110a, 110b may provide a text field in the contributor dashboard in which the contributor may textually enter the dietary goal recommendation for the selected participant. The nutrition program 110a, 110b may provide the contributor with the option to submit the dietary goal recommendation, for example, by clicking a "Submit" button in the contributor dashboard.

In one embodiment, the contributor may include a doctor. The dietary goal recommendation received from the doctor may be related to a health treatment and/or a prophylactic measure for the selected participant (e.g., a patient). In one embodiment, the contributor may include a teacher. The dietary goal recommendation received from the teacher may be related to a nutrition education lesson, awareness project, and/or other school effort intended for the selected participant group (e.g., class of students). In one embodiment, the contributor may include a third-party service (e.g., amusement park, toy store, theater, social/religious organization, government entity, civil association). The dietary goal recommendation received from the third-party service may be related to a campaign to raise nutrition awareness in the selected participant group (e.g., participants ages 5 to 7).

In at least one embodiment, the nutrition program 110a, 110b may also provide the moderator with one or more automatically generated dietary goal recommendations for the participant. The dietary goal recommendations provided by the nutrition program 110a, 110b may be calculated based on considerations of the health information and nutritional history of the participant and the nutritional recommendations made by doctors and public health organizations for children who share common characteristics (e.g., gender, age, height, weight) with the participant. In one embodiment, the nutrition program 110a, 110b may retrieve nutritional guidelines or recommendations for a population (e.g., children) that shares similarities with the participant. The nutrition program 110a, 110b may then compare the nutritional guidelines or recommendations against the nutritional history of the participant. If the nutrition program 110a, 110b determines a nutritional gap (e.g., required nutrients being overlooked, irregular eating schedule, unhealthy or high caloric foods ingested above the recommended threshold) in the nutrition history of the participant, the nutrition program 110a, 110b may automatically generate the dietary goal recommendations and provide the dietary goal recommendations in the moderator dashboard.

After receiving (e.g., via communication network 116) the submitted dietary goal recommendation from the contributor device, the nutrition program 110a, 110b may determine the intended participant for the dietary goal recommendation and may transmit (e.g., via communication network 116) the dietary goal recommendation to the moderator profile linked to the participant user profile of the of the intended participant. Specifically, the nutrition program 110a, 110b may provide or list the dietary goal recommendation in the moderator dashboard of the moderator. The nutrition program 110a, 110b may provide the moderator with the option to accept/approve the dietary goal recommendation for the participant by selecting the dietary goal recommendation (e.g., via clicking the adjacent check box) and clicking a "Submit" button in the moderator dashboard.

In one example, the moderator may be a parent and the participant may be a child of the parent. The parent running the nutrition program 110a, 110b on a parent device may log in to a parent user profile by textually entering, in a log in page of the nutrition program 110a, 110b, the username and password associated with the parent user profile. After verifying the entered credentials of the parent user profile, the nutrition program 110a, 110b may direct the parent to the moderator dashboard where the nutrition program 110a, 110b may display three dietary goal recommendations for the child. A first dietary goal recommendation may be received from a first contributor, for example, the teacher of the child. A second dietary goal recommendation may be received from a second contributor, for example, the doctor of the child. A third dietary goal recommendation may be automatically generated by the nutrition program 110a, 110b.

The teacher may access the contributor dashboard by running the nutrition program 110a, 110b on a teacher device and logging in to a teacher user profile with a username and password associated with the teacher user profile. The teacher may enter the first dietary goal into a text field provided in the contributor dashboard. The first dietary goal recommendation may propose, for example, eating ten servings of vegetables. The nutrition program 110a, 110b may receive the first dietary goal recommendation from the teacher device via communication network 116.

The doctor may access the contributor dashboard by running the nutrition program 110a, 110b on a doctor device and logging in to a doctor user profile with a username and password associated with the doctor user profile. The doctor may enter the second dietary goal into the text field provided in the contributor dashboard. The second dietary goal recommendation may propose, for example, substituting water for soda for a fourteen-day period. The nutrition program 110a, 110b may receive the second dietary goal recommendation from the doctor device via communication network 116.

The nutrition program 110a, 110b may learn, from historical participant nutritional data stored with the participant user profile, that the participant skips breakfast. Based on that finding, the nutrition program 110a, 110b may automatically generate the third dietary goal recommendation, proposing, for example, eating a healthy breakfast for a fourteen-day period.

The nutrition program 110a, 110b may display, in the moderator dashboard, the three dietary goal recommendations proposed for the child, as well as a text field for receiving a parent created dietary goal for the child. The parent may approve the first dietary goal recommendation from the teacher by clicking the check box adjacent the first dietary goal recommendation. Thereafter, the parent may click a "Submit" button in the moderator dashboard to transmit the approved dietary goal from the parent device to the nutrition program 110a, 110b via communication network 116.

Then, at 204, the approved dietary goal is transmitted to a digital entity. The nutrition program 110a, 110b may provide the digital entity as the primary interface between the nutrition program 110a, 110b and the participant. The digital entity may include a virtual avatar selected and personalized by the participant or the moderator. The virtual avatar may, for example, include a representation of an animal, a flower, a toy, a game/cartoon character, an emoji, or any animated character. The participant may run the nutrition program 110a, 110b on a participant device (e.g., a tablet device) to engage the digital entity within a gamified interface. The transmitted dietary goal may be received by the participant via the digital entity at 302 of a participant process 300, as will be further detailed with reference to FIG. 3. The nutrition program 110a, 110b may transmit (e.g., via communication network 116) the dietary goal to the participant device. Additionally, in one embodiment, the nutrition program 110a, 110b may also transmit (e.g., via communication network 116) an indication of the reward (e.g., digital entity evolution, digital badge) that the participant may receive for accomplishing the dietary goal.

According to one embodiment, the virtual avatar may interact with the child through textual, visual, and audio feedback. The interactions between the virtual avatar and the child may vary based on the age, gender, cultural characteristics (e.g., country, language, religion/belief), and social/developmental characteristics (e.g., Autism, Asperger's Syndrome) of the child. Through the interactions between the virtual avatar and the child, the digital entity may provide the food ingestion recommendations directly associated with the dietary goals created or approved by the parent/caregiver and may depict the virtual evolution of the digital entity (e.g., increase in size, strength, format, color, health).

The nutrition program 110a, 110b may enable the digital entity to interact with the participant via textual, visual, and audio feedback. In one embodiment, the nutrition program 110a, 110b may provide, via interactions between the participant and the digital entity, one or more instructions (e.g., via a dialog box in the gamified interface) for completing the dietary goal created or approved by the moderator. In at least one embodiment, the digital entity may indicate food recommendations (e.g., via a dialog box) associated with the dietary goal created or approved by the moderator.

Continuing with the previous example, the nutrition program 110a, 110b transmits, via communication network 116, the approved dietary goal to the tablet device used by the child. The nutrition program 110a, 110b transmits a textual/visual/audio notification via the digital entity indicating that a new dietary goal challenge is available for the child. Specifically, the nutrition program 110a, 110b displays a dialog box from the digital entity which instructs the child to eat ten servings of vegetables. The dialog box from the digital entity also indicates that, by completing the dietary goal challenge, the child will receive a predetermined reward of a 100 health points towards the evolution of the digital entity.

Then, at 206, evidence of the participant diet is received. The participant and/or the moderator may input evidence of the participant diet at 304 of the participant process 300, as will be further detailed with reference to FIG. 3. The nutrition program 110a, 110b may receive (e.g., via communication network 116) evidence from, for example, an image capturing device (e.g., a tablet device camera) used by the participant and/or the moderator. The evidence may be provided in an image (e.g., .jpeg) or a video format (e.g., .mpeg). In one embodiment, the nutrition program 110a, 110b may receive a first photo of a food/drink before the food/drink is ingested by the participant. In another embodiment, the nutrition program 110a, 110b may also receive a second photo of the food/drink if there are leftovers of the food/drink which the participant did not finish. In at least one embodiment, the nutrition program 110a, 110b may receive manual inputs (e.g., textually via the dashboard) indicating the type and quantity of the food/drink ingested by the participant and when the food/drink was ingested by the participant (e.g., hour of the day). It is also contemplated that the nutrition program 110a, 110b may receive evidence in any suitable manner (e.g., barcode scanner, QR scanner).

In one embodiment, the nutrition program 110a, 110b may include a cognitive component having artificial intelligence capabilities, machine learning capabilities, visual recognition capabilities, and other suitable cognitive algorithms. The nutrition program 110a, 110b may deploy the cognitive component to analyze the received photos. Specifically, the nutrition program 110a, 110b may implement the visual recognition capabilities, artificial intelligence capabilities, and machine learning capabilities to recognize the food/drink in the photo and to identify specific characteristics, such as the size of the food/drink portion. In one embodiment, the nutrition program 110a, 110b may provide a nutrition-related database. The nutrition program 110a, 110b may access (e.g., via communication network 116) the nutrition-related database to compare the received photos with the food/drink images stored in the nutrition-related database. Based on the comparison of the received photos and the images stored in the nutrition-related database, the cognitive component of the nutrition program 110a, 110b may identify the food/drink depicted in the received photos. In one embodiment, the nutrition program 110a, 110b may access the nutrition-related database to retrieve nutrition information (e.g., calories, sugar, fat, protein) associated with the food/drink identified by the cognitive component in the received photos. Based on the before and after photos of the food/drink, the nutrition program 110a, 110b may deploy the cognitive component to calculate the specific consumed nutrient information based on the quantity of the food/drink consumed by the participant and the nutrition information retrieved from the nutrition-related database about the identified food/drink consumed by the participant.

According to one embodiment, the nutrition program 110a, 110b may prompt the participant and/or the moderator to verify the accuracy of the food/drink recognized in the photos (e.g., via a dialog box with a "Yes" and a "No" button, or with another suitable visual/textual/audible prompt to the participant, like a question from the digital entity) by the cognitive component. If the nutrition program 110a, 110b is unable to accurately recognize the food/drink depicted in the photos, the nutrition program 110a, 110b may provide the participant/moderator with the option to textually enter the type and quantity of the food/drink depicted in the photos. The nutrition program 110a, 110b may utilize the feedback from the participant/moderator to train the cognitive component of the nutrition program 110a, 110b.

Continuing with the previous example, the nutrition program 110a, 110b receives, via communication network 116, a photo from the tablet device camera used by the child. The received photo is a .jpeg file depicting an image of a lunch prepared for the child. The nutrition program 110a, 110b analyzes the received photo using the visual recognition capabilities, artificial intelligence capabilities, machine learning capabilities, and other cognitive algorithms of the cognitive component. The nutrition program 110a, 110b interacts with the nutrition-related database via communication network 116 to compare the images stored in the nutrition-related database with the photo received from the tablet device camera. Based on the analysis of the cognitive component and the interaction with the nutrition-related database, the nutrition program 110a, 110b recognizes one serving of chicken, one serving of broccoli, and one serving of rice in the received photo.

Then, at 208, the participant diet is recorded. The nutrition program 110a, 110b may record the consumed nutrient information determined from the participant diet after every entry received at 206. In one embodiment, the nutrition program 110a, 110b may generate a nutrition history repository associated with the participant user profile. The nutrition program 110a, 110b may record the consumed nutrient information determined from the participant diet into the nutrition history repository. In one embodiment, the consumed nutrient information recorded by the nutrition program 110a, 110b may include the type of food/drink consumed (e.g., fruits, vegetables, protein, water, juice), the type of nutrients consumed, the serving/quantity consumed, and the type of meal (e.g., breakfast, lunch, dinner, snack). In one embodiment, the nutrition program 110a, 110b may also record when the food/drink was consumed (e.g., date and time) and where the food/drink was consumed, if a geolocation option is enabled and approved by the moderator or the participant. The nutrition program 110a, 110b may store or provide the nutrition history repository within the database 114 of the server 112 and may communicate with the nutrition history repository via the communication network 116.

Continuing with the previous example, the nutrition program 110a, 110b generates a nutrition history repository associated with the participant user profile of the child in the database 114. After determining, from the photo received at 206, that the child consumed one serving of chicken, one serving of broccoli, and one serving of rice for lunch, the nutrition program 110a, 110b communicates with the nutrition history repository of the child via communication network 116 and records the consumed nutrient information in the nutrition history repository.

Then, at 210, the nutrition program 110a, 110b determines if the goal is accomplished. The nutrition program 110a, 110b may determine that the dietary goal is accomplished by the participant if a dietary goal progression of the participant meets or exceeds the requirements of the dietary goal. On the other hand, the nutrition program 110a, 110b may determine that the dietary goal is not accomplished by the participant if the dietary goal progression of the participant does not meet the requirements of the dietary goal. The nutrition program 110a, 110b may calculate the dietary goal progression of the participant by retrieving (e.g., via communication network 116) an aggregate nutrition history of the participant from the nutrition history repository. The nutrition program 110a, 110b may generate the aggregate nutrition history based on the recent and pre-existing consumed nutrient information of the participant. The nutrition program 110a, 110b may then compare the aggregate nutrition history of the participant against the dietary goal of the participant. In one embodiment, the nutrition program 110a, 110b may indicate the dietary goal progression using a score which may be updated (e.g., increased or decreased) to reflect the progression. In one embodiment, the nutrition program 110a, 110b may transmit (e.g., via communication network 116) the score for the dietary goal progression to the digital entity.

According to one embodiment, the nutrition program 110a, 110b may consider additional participant metrics when calculating the dietary goal progression. The additional participant metrics may include, for example, participant health conditions, eating disorders, and food allergies/intolerances. The nutrition program 110a, 110b may weigh the participant metrics differently according to, for example, a health impact to the participant and/or a medical recommendation for the participant.

If the nutrition program 110a, 110b determines that the dietary goal is not accomplished at 210, the nutrition program 110a, 110b will update the participant user profile at 214. In one embodiment, the nutrition program 110a, 110b may record the status of the dietary goal progression in the participant user profile. The nutrition program 110a, 110b may also transmit (e.g., via communication network 116) the status of the dietary goal progression to the moderator (e.g., via the moderator dashboard) and to the contributor (e.g., via the contributor dashboard) associated with the dietary goal recommendation. The contributor may then update a contributor record (e.g., school record, medical record) to indicate the status of the dietary goal progression of the participant.

According to one embodiment, the nutrition program 110a, 110b may track the dietary goal progression for a system-defined period of time to determine if the dietary goal will be accomplished by the participant. If the nutrition program 110a, 110b determines that the dietary goal may not be accomplished by the participant, the nutrition program 110a, 110b may generate associated recommendations for the moderator to facilitate accomplishment of the dietary goal by the participant. The nutrition program 110a, 110b may provide associated recommendations including alternative food sources, preparation recipes, eating sequence/food combinations, and other suitable instructions or directions. The nutrition program 110a, 110b may transmit (e.g., via communication network 116) the associated recommendations to the moderator via the moderator dashboard.

Continuing with the previous example, the nutrition program 110a, 110b retrieves, via communication network 116, an aggregate nutrition history of the child from the nutrition history repository associated with the participant user profile of the child. The aggregate nutrition history of the child indicates that the child has ingested seven servings of vegetables following the start of the dietary goal instructing the child to eat ten servings of vegetables. The nutrition program 110a, 110b then compares the recorded seven servings of vegetables ingested by the participant against the dietary goal of ten servings of vegetables and determines that the dietary goal progression of the child is 70%. Accordingly, the nutrition program 110a, 110b determines that the dietary goal is not accomplished by the child. Thereafter, the nutrition program 110a, 110b records the status of the dietary goal progression of 70% in the participant user profile. The nutrition program 110a, 110b also transmits, via communication network 116, the status of the dietary goal progression to the dashboard of the parent and the dashboard of the teacher who submitted the dietary goal recommendation.

If the nutrition program 110a, 110b determines that the dietary goal is accomplished at 210, the nutrition program 110a, 110b will release the reward for the accomplished goal at 212. Thereafter, the released reward may be received by the participant at 306 of the participant process 300, as will be further detailed with reference to FIG. 3.

In one embodiment, the reward released to the participant for the dietary goal accomplishment may include an update to the digital entity. The nutrition program 110a, 110b may transmit (e.g., via communication network 116) the update for the digital entity to the participant user device. In one embodiment, the nutrition program 110a, 110b may update the digital entity by providing the participant with enhancements (e.g., badges, accessories, health/experience points, evolutionary step) for the digital entity. In at least one embodiment, the reward released to the participant for the dietary goal accomplishment may include digital content (e.g., a badge, an ornament, a status message) which the participant may share on a social media network. The nutrition program 110a, 110b may generate the digital content (e.g., badge, ornament, status message) indicating the dietary goal accomplishment of the participant and may transmit (e.g., via communication network 116) the digital content to the participant user device. In another embodiment, the reward released to the participant for the dietary goal accomplishment may include a claim for a third-party reward. The third-party reward may include, for example, rights to redeem discounts, earn gifts/amenities/privileges, or other material goods from a third-party service. The nutrition program 110a, 110b may transmit (e.g., via communication network 116) the claim (e.g., a digital reward voucher, promotion code) to the participant user device, which the participant may then provide to the third-party service (e.g., via a third-party portal) to redeem the third-party reward.

Continuing with the previous example, the nutrition program 110a, 110b retrieves, via communication network 116, the aggregate nutrition history of the child from the nutrition history repository which indicates that the child has consumed ten servings of vegetables following the start of the dietary goal. The nutrition program 110a, 110b then compares the recorded ten servings of vegetables consumed by the child against the dietary goal of ten servings of vegetables and determines that the dietary goal progression of the child is 100%. Accordingly, the nutrition program 110a, 110b determines that the dietary goal is accomplished by the child at 210. Thereafter, the nutrition program 110a, 110b releases the predetermined reward of 100 health points towards the evolution of the digital entity. The nutrition program 110a, 110b transmits, via the communication network 116, the 100 health points for the digital entity of the child to the tablet device of the child.

After the nutrition program 110a, 110b releases the reward for the accomplished goal at 212, or if the nutrition program 110a, 110b determines that the dietary goal is not accomplished at 210, then, at 214, the participant user profile is updated. In one embodiment, the nutrition program 110a, 110b may record the status of the dietary goal progression (e.g., that the dietary goal is accomplished) in the participant user profile. The nutrition program 110a, 110b may also transmit (e.g., via communication network 116) the status of the dietary goal progression to the moderator (e.g., via the moderator dashboard) and to the contributor (e.g., via the contributor dashboard) associated with the dietary goal recommendation. The contributor may then update the contributor record (e.g., school record, medical record) to indicate the dietary goal accomplishment of the participant.

Continuing with the previous example, the nutrition program 110a, 110b updates the participant user profile of the child to record that the dietary goal is accomplished by the child. The nutrition program 110a, 110b also transmits, via communication network 116, the status of the dietary goal progression (that the dietary goal is accomplished) to the moderator dashboard of the parent and to the contributor dashboard of the teacher who submitted the dietary goal recommendation. The teacher then updates the school record to indicate the dietary goal accomplishment of the child.

Figure 3:
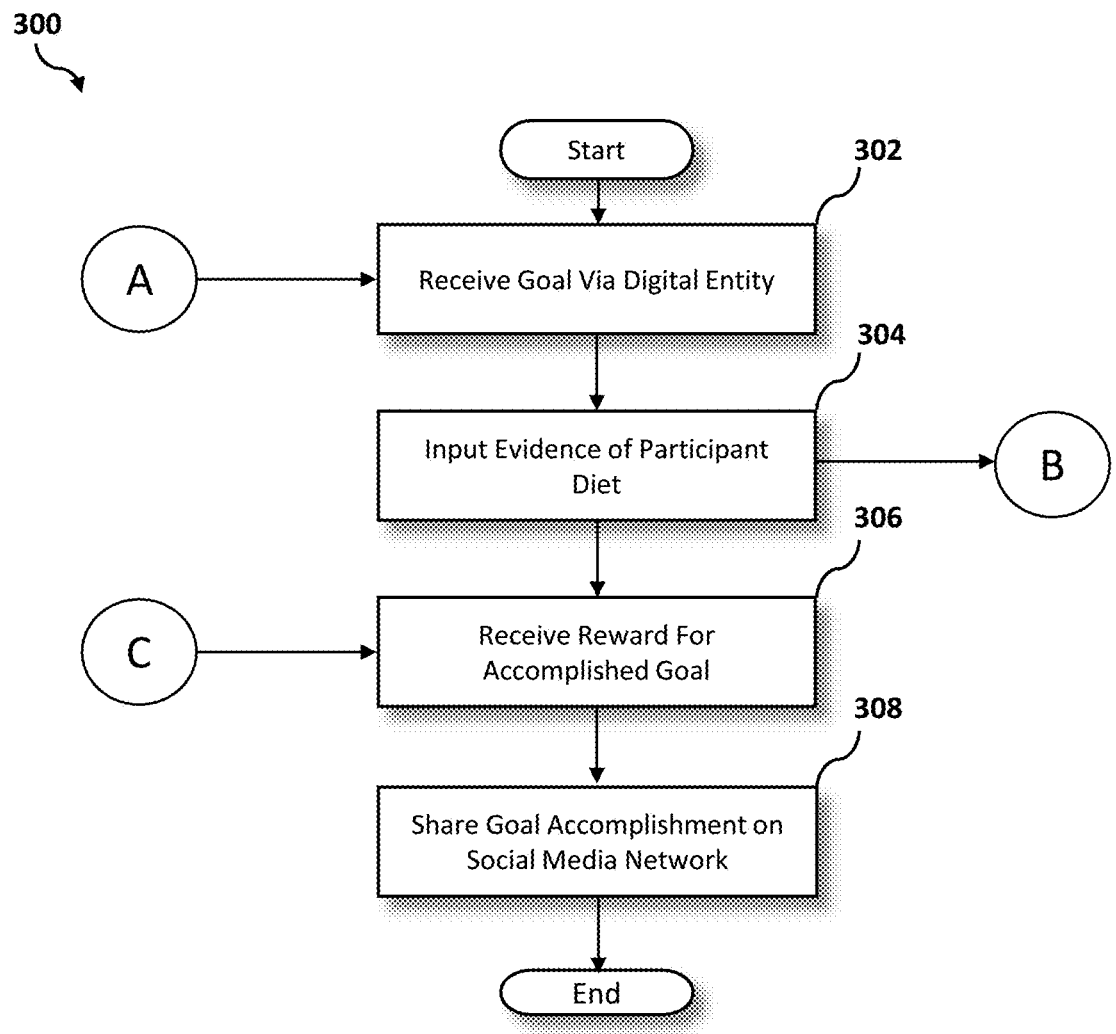
FIG. 3 is an operational flowchart illustrating a process for a participant interaction in the reward-based nutrition process according to at least one embodiment.

Referring now to FIG. 3, an operational flowchart illustrating the exemplary participant process 300 used by the nutrition program 110a, 110b according to at least one embodiment is depicted.

At 302, the goal is received via the digital entity. According to one embodiment, the digital entity may serve as the primary interface between the nutrition program 110a, 110b and the participant. The participant may use the participant user device (e.g., client computer 102) to interact with the digital entity in the gamified interface provided by the nutrition program 110a, 110b. The nutrition program 110a, 110b, via the gamified interface, may enable the participant to select and personalize the digital entity. After the nutrition program 110a, 110b transmits (e.g., via communication network 116) the approved dietary goal, as previously detailed at 204, the digital entity of the participant may receive the dietary goal. In one embodiment, the digital entity may display (e.g., via a dialog box) the dietary goal as a challenge with an associated reward. In at least one embodiment, the digital entity may provide instructions (e.g., food recommendations) for accomplishing the dietary goal. In another embodiment, the digital entity may also provide alerts, reminders, and other notifications to the participant (e.g., "it is time to drink a cup of water"). According to one embodiment, the digital entity may also provide nutrition education associated with the health benefits of the dietary goal.

For example, the child engages with the gamified interface running on the tablet device of the child. The gamified interface provides a selection page including various digital entities from which the child may select the digital entity. The child interacts with the tablet device and chooses a tiger cub as the digital entity from the selection page. The gamified interface receives the dietary goal from the nutrition program 110a, 110b via the communication network 116 and notifies the child via a dialog box from the tiger cub that a new dietary goal challenge is available. The dialog box includes text instructing the child to eat ten servings of vegetables and to provide evidence of doing so. The dialog box also includes text indicating that the child will receive 100 health points for the tiger cub after the dietary goal is accomplished. Further, the dialog box includes text indicating that the child can evolve the tiger cub with the 100 health points.

Then, at 304, evidence of the participant diet is inputted. The participant may follow the requirements of the dietary goal and may provide evidence in the format of photos and videos. The evidence of the participant diet may be received by the nutrition program 110a, 110b as previously detailed at 206. According to one embodiment, the evidence may be collected by the participant and/or the moderator (e.g., the parent) using an image capturing device (e.g., tablet device camera) and may be uploaded (e.g., via communication network 116) to the nutrition program 110a, 110b from the participant user device and/or the moderator device. In one embodiment, the image capturing device may be internet enabled such that the captured photos and videos may be automatically uploaded to the nutrition program 110a, 110b. In at least one embodiment, the contributors (e.g., teacher, doctors) may access the respective contributor dashboard to manually input information about the participant diet (e.g., type of food, serving/quantity, date/time), which may then be transmitted (e.g., via communication network 116) to the nutrition program 110a, 110b.

Continuing with the previous example, the child follows the dietary goal requirement of eating ten servings of vegetables. The child inputs evidence of the diet by taking a photo of the meals eaten by the child. Specifically, the child uses the tablet device camera to capture a photo of a lunch meal including chicken, broccoli, and rice. The photo is automatically uploaded from the tablet device to the nutrition program 110a, 110b, via the communication network 116, as evidence of the diet followed by the child.

Then, at 306, the reward for the accomplished goal is received. After the participant accomplishes the dietary goal and the nutrition program 110a, 110b releases the reward for the accomplished dietary goal, as previously detailed at 212, the participant may receive the reward via the gamified interface running on the participant user device. In one embodiment, the digital entity in the gamified interface may provide textual, visual, or audio feedback notifying the participant of the dietary goal accomplishment and the received reward.

Continuing with the previous example, after the child eats ten servings of vegetables to accomplish the dietary goal, the digital entity in the gamified interface displays a congratulatory visual feedback to notify the child that the dietary goal is accomplished. The digital entity also notifies the child that 100 health points is received and available towards the evolution of the digital entity.

Then, at 308, the goal accomplishment is shared on a social media network. The gamified interface may provide an option for the participant to share the dietary goal accomplishment on a social media network. In one embodiment, the gamified interface may provide a "Share" button which the participant may click to share digital content indicating the dietary goal accomplishments of the participant. The digital content may be generated by the nutrition program 110a, 110b and may include, badges, ornaments, ribbons, accessories, status messages, and visual enhancements for the digital entity. After the participant clicks the "Share" button by interacting with the participant user device, the digital content may be shared (e.g., via communication network 116) to the social media network.

Continuing with the previous example, the gamified interface displays a "+100 health points!" badge generated by the nutrition program 110a, 110b. The gamified interface provides a "Share" button and prompts the child, via a dialog box, to click the "Share" button to share the badge on the social media network. The child interacts with the tablet device to click the "Share" button to share the badge on the social media network.

Figure 4:
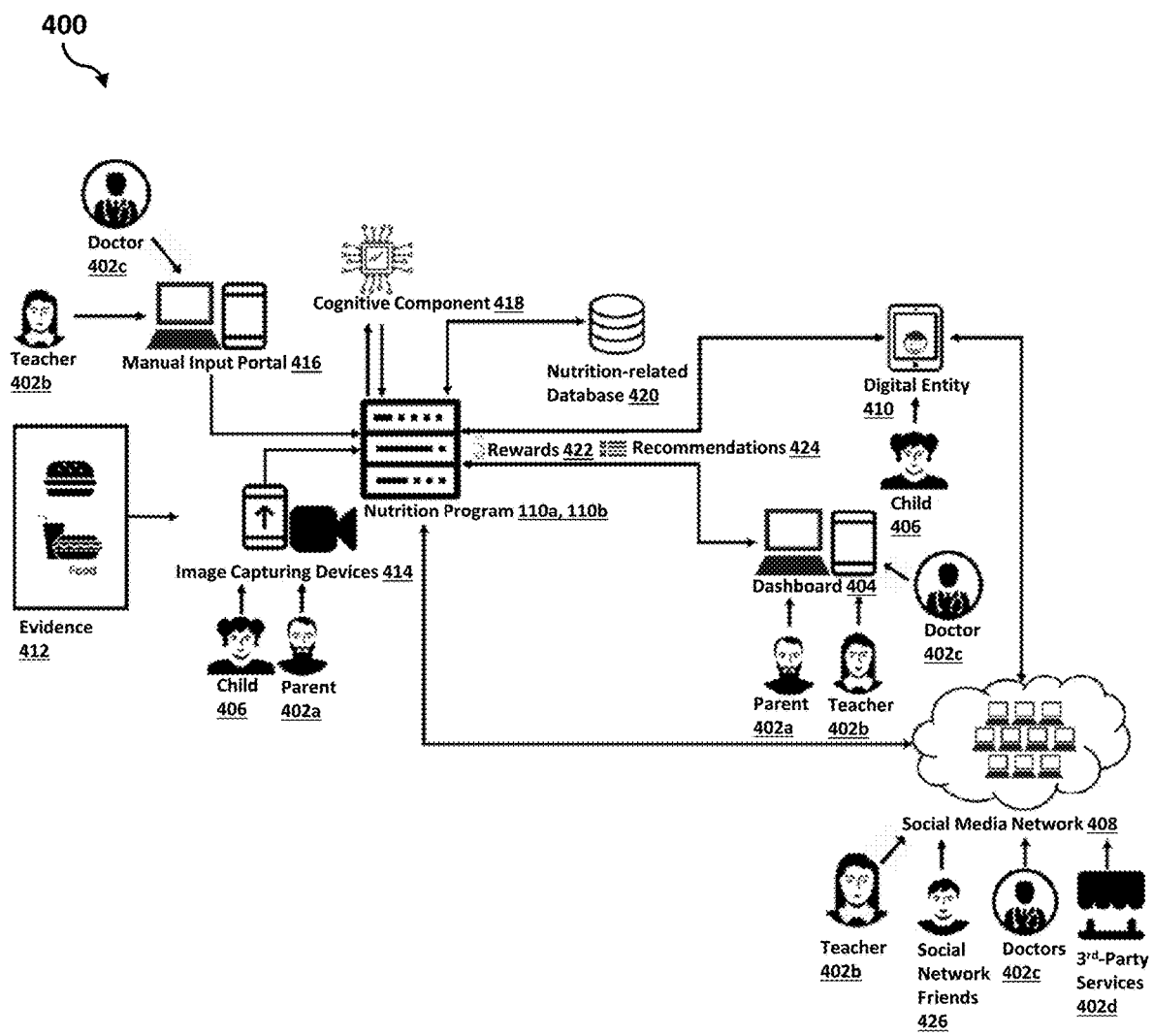
FIG. 4 is an exemplary illustration of a reward-based ecosystem according to at least one embodiment.

Referring now to FIG. 4, an exemplary illustration of a reward-based ecosystem 400 according to at least one embodiment is depicted. The reward-based ecosystem 400 may include the nutrition program 110a, 110b. A parent 402a, a teacher 402b, and a doctor 402c may access the nutrition program 110a, 110b via a respective dashboard 404 to create a dietary goal recommendation for a child 406, as detailed previously at 202. In one embodiment, the reward-based ecosystem 400 may provide a social media network 408 which may communicate with the nutrition program 110a, 110b. The teacher 402b, the doctor 402c, and a third-party service 402d may submit, via the social media network 408, the dietary goal recommendation for the child 406. The dietary goal recommendations from the teacher 402b, the doctor 402c, and the third-party service 402d may be displayed on the dashboard 404 of the parent 402a by the nutrition program 110a, 110b. The parent 402a may access the dashboard 404 to accept/approve one or more of the dietary goal recommendations submitted by the teacher 402b, the doctor 402c, and the third-party service 402d.

The nutrition program 110a, 110b may transmit the dietary goal, approved or created by the parent 402a, to the child 406 via a digital entity 410, as detailed previously at 204. The digital entity 410 may display the dietary goal challenge and an associated reward within a gamified interface running on a participant user device, as detailed previously at 302.

In following the requirements of the dietary goal, the child 406 and/or the parent 402a may input an evidence 412 of the diet (e.g., foods/drinks) being consumed by the child 406, as detailed previously at 304. The evidence 412 may include photos and videos taken by the child 406 and/or the parent 402a using an image capturing device 414. The evidence 412 may be uploaded and received by the nutrition program 110a, 110b, as detailed previously at 206. In one embodiment, additional or eventual users, such as, the teacher 402b and the doctor 402c may access a manual input portal 416 via the respective dashboard 404 to textually input information associated with the diet consumed by the child 406 (e.g., types of foods, serving size, date/time).

According to one embodiment, the reward-based ecosystem 400 may provide a cognitive component 418 to the nutrition program 110a, 110b. The cognitive component 418 may include artificial intelligence algorithms, machine learning algorithms, and visual recognition capabilities to identify the food/drink items in the evidence 412 received at 206. The reward-based ecosystem 400 may also provide a nutrition-related database 420 which the nutrition program 110a, 110b may interact with in order to retrieve the nutrition information about the foods/drinks consumed by the child 406 and to calculate, using the cognitive component 418, the amount of nutrients consumed by the child 406 in each meal.

In one embodiment, the nutrition program 110a, 110b may record the nutrition information gathered from the evidence 412, as detailed previously at 208, and may determine, based on the recorded nutrition information, if the dietary goal is accomplished by the child 406, as detailed previously at 210. If the nutrition program 110a, 110b determines that the dietary goal is accomplished by the child 406, the nutrition program 110a, 110b may release a reward 422 for the accomplished dietary goal. In one embodiment, the reward 422 may be a digital content (e.g., ornaments, ribbons, visual enhancements for the digital entity) generated by the nutrition program 110a, 110b. In at least one embodiment, the child 406 may share the digital content received from the nutrition program 110a, 110b via the social media network 408 with one or more social network friends 426. In another embodiment, if the dietary goal is submitted by or associated with the third-party service 402d, the reward 422 released by the nutrition program 110a, 110b may be a voucher or promotional code to redeem a third-party reward.

However, if the nutrition program 110a, 110b determines that the dietary goal may not be accomplished by the child 406, as detailed previously at 210, the nutrition program 110a, 110b may provide one or more recommendations 424 to the parent 402a to increase the success rate of the child 406 accomplishing the dietary goal.

As described herein, the nutrition program 110a, 110b may have the capacity to improve the technical field of health and nutrition by engaging a participant to follow one or more prescribed dietary goals in exchange for rewards, incentives, social recognition, and other positive feedback. The nutrition program 110a, 110b may deliver the dietary goals via a gamified interface including pictures, sounds, animations, and other multimedia feedback in a manner that may capture the attention of the participant and may engage the participant to follow the dietary goals. The nutrition program 110a, 110b may provide artificial intelligence capabilities, machine learning capabilities, and visual recognition capabilities to identify the foods and drinks consumed by the participant and to determine if the participant is progressing towards accomplishing the dietary goal. The gamified experience, combined with the rewards, and the social sharing features, may incentivize the participant to develop healthy nutritional habits. Thus, the nutrition program 110a, 110b may improve the functionality of a computer.

It may be appreciated that FIGS. 2-4 provide only an illustration of one embodiment and do not imply any limitations with regard to how different embodiments may be implemented. Many modifications to the depicted embodiment(s) may be made based on design and implementation requirements.

Figure 5:
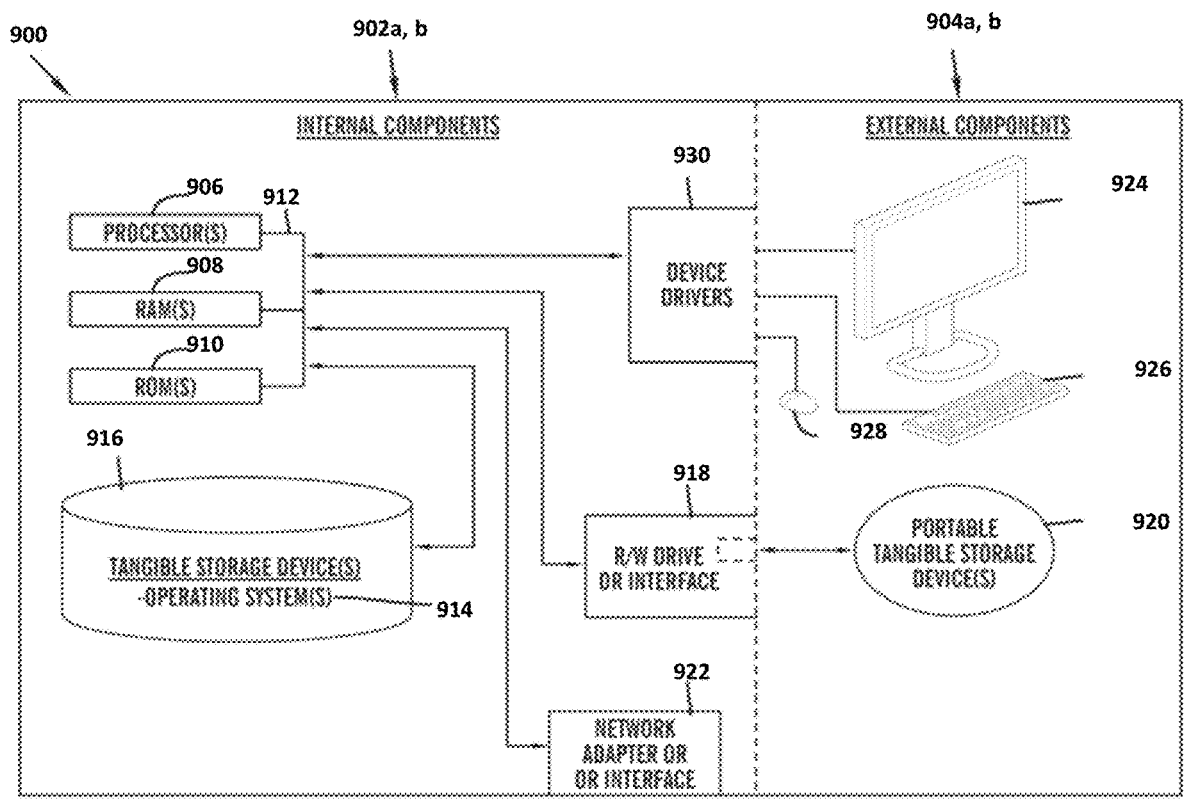
FIG. 5 is a block diagram of internal and external components of computers and servers depicted in FIG. 1 according to at least one embodiment.

FIG. 5 is a block diagram 900 of internal and external components of computers depicted in FIG. 1 in accordance with an illustrative embodiment of the present invention. It should be appreciated that FIG. 5 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902a, b and external components 904a, b illustrated in FIG. 5. Each of the sets of internal components 902a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the nutrition program 110a in client computer 102, and the nutrition program 110b in network server 112, may be stored on one or more computer-readable tangible storage devices 916 for execution by one or more processors 906 via one or more RAMs 908 (which typically include cache memory). In the embodiment illustrated in FIG. 5, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the nutrition program 110a, 110b can be stored on one or more of the respective portable computer-readable tangible storage devices 920, read via the respective R/W drive or interface 918 and loaded into the respective hard drive 916.

Each set of internal components 902a, b may also include network adapters (or switch port cards) or interfaces 922 such as a TCP/IP adapter cards, wireless wi-fi interface cards, or 3G or 4G wireless interface cards or other wired or wireless communication links. The software program 108 and the nutrition program 110a in client computer 102 and the nutrition program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the nutrition program 110a in client computer 102 and the nutrition program 110b in network server computer 112 are loaded into the respective hard drive 916. The network may comprise copper wires, optical fibers, wireless transmission, routers, firewalls, switches, gateway computers and/or edge servers.

Each of the sets of external components 904a, b can include a computer display monitor 924, a keyboard 926, and a computer mouse 928. External components 904a, b can also include touch screens, virtual keyboards, touch pads, pointing devices, and other human interface devices. Each of the sets of internal components 902a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
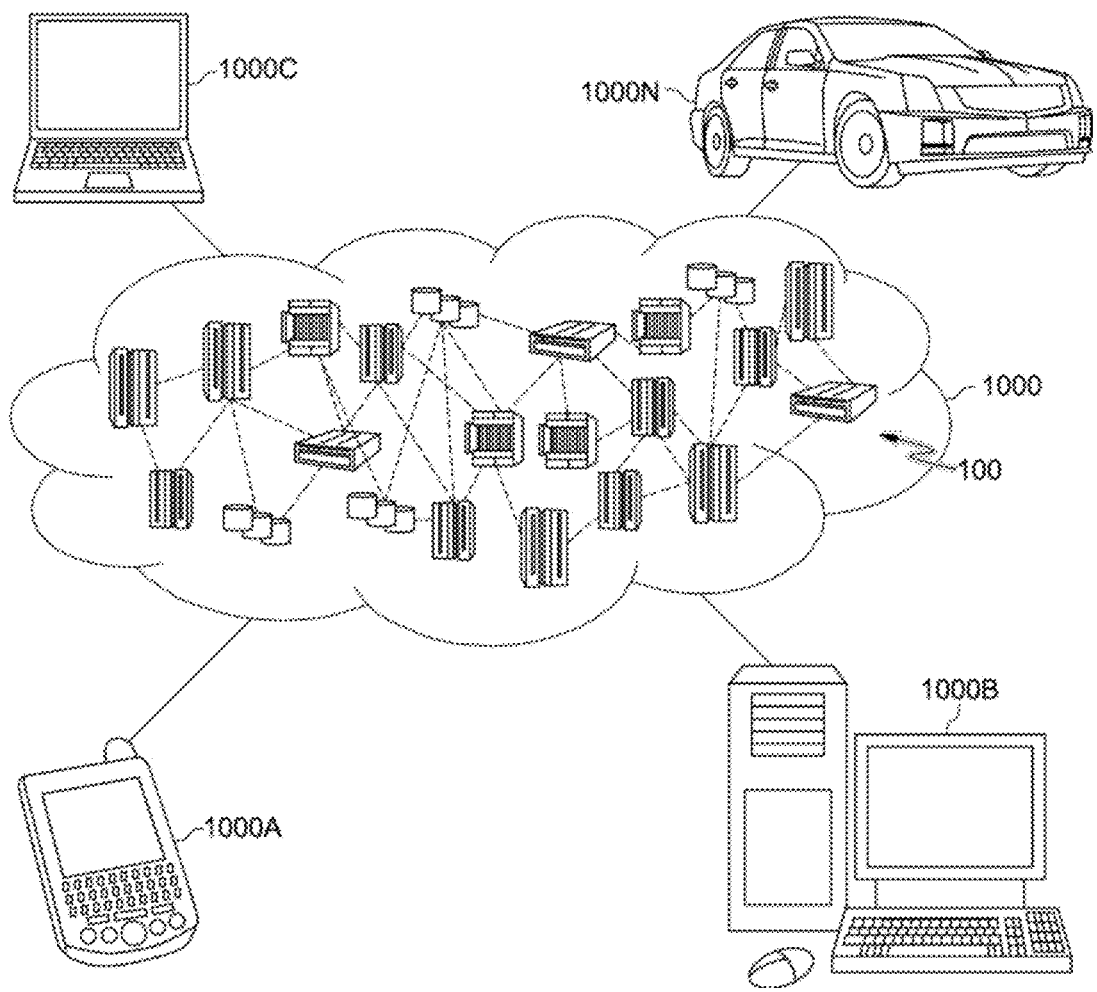
FIG. 6 is a block diagram of an illustrative cloud computing environment including the computer system depicted in FIG. 1, in accordance with an embodiment of the present disclosure.

Referring now to FIG. 6, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 6 are intended to be illustrative only and that computing nodes 100 and cloud computing environment 1000 can communicate with any type of computerized device over any type of network and/or network addressable connection (e.g., using a web browser).

Figure 7:
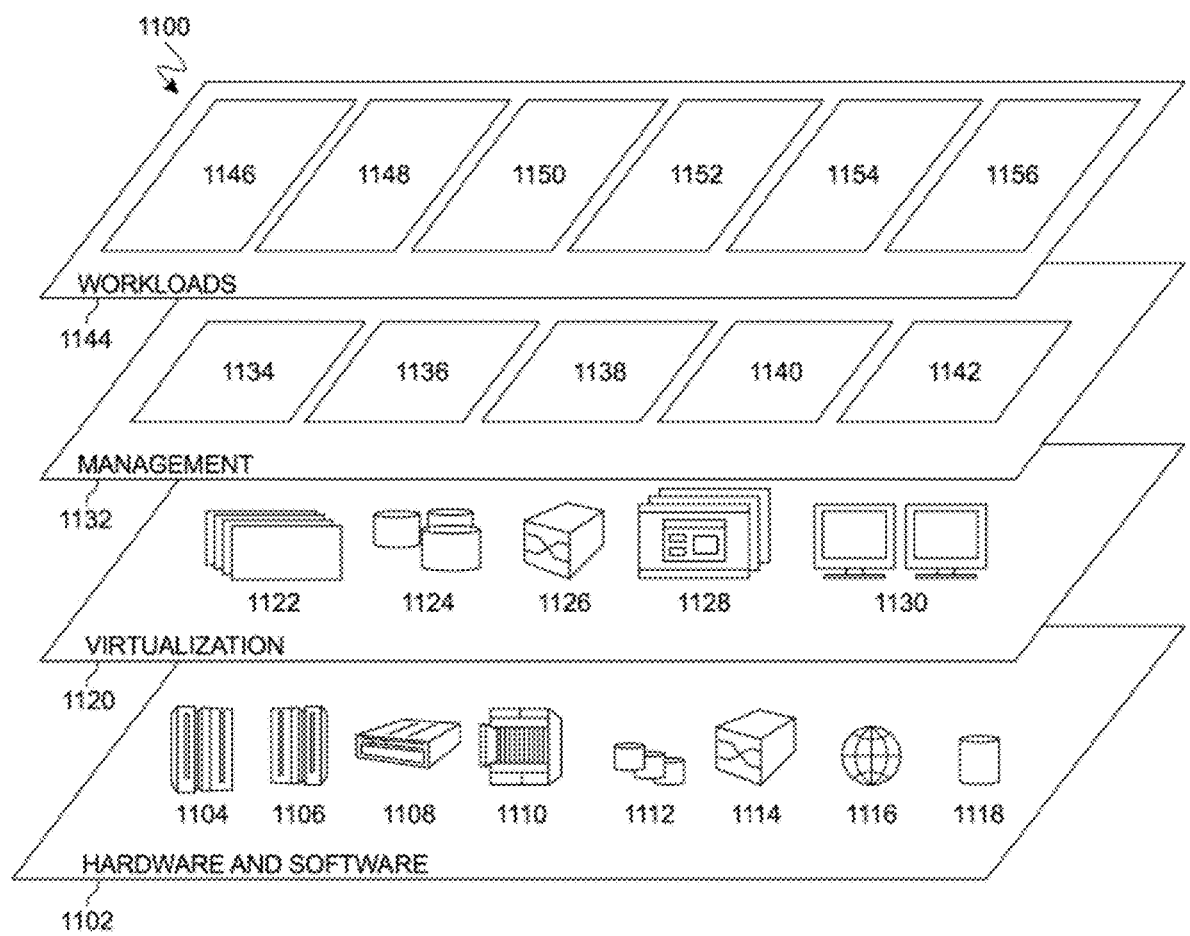
FIG. 7 is a block diagram of functional layers of the illustrative cloud computing environment of FIG. 6, in accordance with an embodiment of the present disclosure.

Referring now to FIG. 7, a set of functional abstraction layers 1100 provided by cloud computing environment 1000 is shown. It should be understood in advance that the components, layers, and functions shown in FIG. 7 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and reward-based nutrition goal delivery 1156. A nutrition program 110a, 110b provides a way to improve the nutritional consumption of a participant through reward-based dietary goals.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for tracking a nutritional consumption, the method comprising:
   providing a digital avatar associated with a participant;
   transmitting a dietary goal to a device associated with the digital avatar, wherein the transmitted dietary goal includes a nutritional requirement for the participant;
   recognizing at least one food item consumed by the participant;
   determining a consumed nutrient information associated with the recognized at least one food item consumed by the participant;
   in response to determining that the nutritional requirement of the transmitted dietary goal is met by the determined consumed nutrient information, releasing a reward to the device associated with the digital avatar, wherein the released reward is associated with an accomplishment of the dietary goal by the participant;
   in response to the released reward, depicting, in the device associated with the digital avatar, a virtual evolution of the digital avatar; and
   determining an ability of the participant to understand long term objectives,
   wherein the virtual evolution of the digital avatar is based on the ability of the participant to understand the long term objectives and the ability determines a timing of evolutionary steps of the virtual evolution in engaging the participant.

2. The method of claim 1, further comprising:
   receiving a dietary goal recommendation for the participant from a contributor associated with the participant;
   providing a first option for a moderator associated with the participant to approve the received dietary goal recommendation for the participant;
   providing a second option for the moderator to submit a moderator-created dietary goal recommendation for the participant;
   in response to the moderator approving the received dietary goal recommendation for the participant, transmitting, to the device associated with the digital avatar, the approved dietary goal recommendation as the dietary goal for the participant; and
   in response to the moderator submitting the moderator-created dietary goal recommendation for the participant, transmitting, to the device associated with the digital avatar, the submitted moderator-created dietary goal recommendation as the dietary goal for the participant.

3. The method of claim 1, further comprising:
retrieving a nutritional guideline provided for a population including at least one common characteristic with the participant;
retrieving a nutritional history of the participant;
comparing the retrieved nutritional guideline for the population including the at least one common characteristic with the participant with the retrieved nutritional history of the participant; and
in response to determining a nutritional gap in the retrieved nutritional history of the participant, generating an automatic dietary goal recommendation for the participant associated with the nutritional gap.

4. The method of claim 1, wherein releasing the reward to the digital avatar, further comprises:
generating a digital content for the participant for sharing on a social media network, wherein the generated digital content is selected from the group consisting of a badge, an ornament, a status message, an enhancement for the digital avatar, and an evolutionary step for the digital avatar; and
providing a voucher for the participant for redeeming a third-party reward, wherein the redeemed third-party reward is selected from the group consisting of a discount, an amenity, and a material good from a third-party service.

5. The method of claim 1, further comprising:
providing a cognitive component, wherein the cognitive component is selected from the group consisting of an artificial intelligence capability, a machine learning capability, and a visual recognition capability;
receiving an evidence of the at least one food item consumed by the participant;
analyzing the received evidence using the cognitive component;
recognizing the at least one food item in the analyzed evidence; and
identifying a quantity of the recognized at least one food item in the analyzed evidence.

6. The method of claim 1, further comprising:
in response to determining that the nutritional requirement of the transmitted dietary goal is not met by the determined consumed nutrient information, recording a status of the dietary goal in a user profile associated with the participant.

7. The method of claim 5, further comprising:
retrieving a plurality of nutritional information associated with the recognized at least one food item from a nutrition-related database; and
calculating the consumed nutrient information based on the retrieved plurality of nutritional information associated with the recognized at least one food item and the identified quantity of the recognized at least one food item.

8. The method of claim 6, further comprising:
monitoring the status of the dietary goal of the participant;
generating a recommendation to meet the nutritional requirement associated with dietary goal by the participant; and
providing the generated recommendation for the participant.

9. A computer system for tracking a nutritional consumption, comprising:
one or more processors, one or more computer-readable memories, one or more computer-readable tangible storage media, and program instructions stored on at least one of the one or more computer-readable tangible storage media for execution by at least one of the one or more processors via at least one of the one or more memories, wherein the computer system is capable of performing a method comprising:
providing a digital avatar associated with a participant;
transmitting a dietary goal to a device associated with the digital avatar, wherein the transmitted dietary goal includes a nutritional requirement for the participant;
recognizing at least one food item consumed by the participant;
determining a consumed nutrient information associated with the recognized at least one food item consumed by the participant;
in response to determining that the nutritional requirement of the transmitted dietary goal is met by the determined consumed nutrient information, releasing a reward to the device associated with the digital avatar, wherein the released reward is associated with an accomplishment of the dietary goal by the participant;
in response to the released reward, depicting, in the device associated with the digital avatar, a virtual evolution of the digital avatar; and
determining an ability of the participant to understand long term objectives,
wherein the virtual evolution is based on the ability of the participant to understand the long term objectives and the ability determines a timing of the released reward in engaging the participant.

10. The computer system of claim 9, further comprising:
receiving a dietary goal recommendation for the participant from a contributor associated with the participant;
providing a first option for a moderator associated with the participant to approve the received dietary goal recommendation for the participant;
providing a second option for the moderator to submit a moderator-created dietary goal recommendation for the participant;
in response to the moderator approving the received dietary goal recommendation for the participant, transmitting, to the device associated with the digital avatar, the approved dietary goal recommendation as the dietary goal for the participant; and
in response to the moderator submitting the moderator-created dietary goal recommendation for the participant, transmitting, to the device associated with the digital avatar, the submitted moderator-created dietary goal recommendation as the dietary goal for the participant.

11. The computer system of claim 9, further comprising:
retrieving a nutritional guideline provided for a population including at least one common characteristic with the participant;
retrieving a nutritional history of the participant;
comparing the retrieved nutritional guideline for the population including the at least one common characteristic with the participant with the retrieved nutritional history of the participant; and
in response to determining a nutritional gap in the retrieved nutritional history of the participant, generating an automatic dietary goal recommendation for the participant associated with the nutritional gap.

12. The computer system of claim 9, wherein releasing the reward to the digital avatar, further comprises:

generating a digital content for the participant for sharing on a social media network, wherein the generated digital content is selected from the group consisting of a badge, an ornament, a status message, an enhancement for the digital avatar, and an evolutionary step for the digital avatar; and providing a voucher for the participant for redeeming a third-party reward, wherein the redeemed third-party reward is selected from the group consisting of a discount, an amenity, and a material good from a third-party service.

13. The computer system of claim 9, further comprising:
providing a cognitive component, wherein the cognitive component is selected from the group consisting of an artificial intelligence capability, a machine learning capability, and a visual recognition capability;
receiving an evidence of the at least one food item consumed by the participant;
analyzing the received evidence using the cognitive component;
recognizing the at least one food item in the analyzed evidence; and
identifying a quantity of the recognized at least one food item in the analyzed evidence.

14. The computer system of claim 9, further comprising:
in response to determining that the nutritional requirement of the transmitted dietary goal is not met by the determined consumed nutrient information, recording a status of the dietary goal in a user profile associated with the participant.

15. The computer system of claim 13, further comprising:
retrieving a plurality of nutritional information associated with the recognized at least one food item from a nutrition-related database; and
calculating the consumed nutrient information based on the retrieved plurality of nutritional information associated with the recognized at least one food item and the identified quantity of the recognized at least one food item.

16. The computer system of claim 14, further comprising:
monitoring the status of the dietary goal of the participant;
generating a recommendation to meet the nutritional requirement associated with the dietary goal by the participant; and
providing the generated recommendation for the participant.

17. A computer program product for tracking a nutritional consumption, comprising:
one or more computer-readable tangible storage media and program instructions stored on at least one of the one or more computer-readable tangible storage media, the program instructions executable by a processor to cause the processor to perform a method comprising:
providing a digital avatar associated with a participant;
transmitting a dietary goal to a device associated with the digital avatar, wherein the transmitted dietary goal includes a nutritional requirement for the participant;
recognizing at least one food item consumed by the participant;
determining a consumed nutrient information associated with the recognized at least one food item consumed by the participant;
in response to determining that the nutritional requirement of the transmitted dietary goal is met by the determined consumed nutrient information, releasing a reward to the device associated with the digital avatar, wherein the released reward is associated with an accomplishment of the dietary goal by the participant;
in response to the released reward, depicting, in the device associated with the digital avatar, a virtual evolution of the digital avatar;
determine an ability of the participant to understand long term objectives,
wherein the virtual evolution is based on the ability of the participant to understand the long term objectives and the ability determines a timing of evolutionary steps of the virtual evolution in engaging the participant;
collect feedback from the participant; and
generate a training data corpus from the collected feedback.

18. The computer program product of claim 17, further comprising:
receiving a dietary goal recommendation for the participant from a contributor associated with the participant;
providing a first option for a moderator associated with the participant to approve the received dietary goal recommendation for the participant;
providing a second option for the moderator to submit a moderator-created dietary goal recommendation for the participant;
in response to the moderator approving the received dietary goal recommendation for the participant, transmitting, to the device associated with the digital avatar, the approved dietary goal recommendation as the dietary goal for the participant; and
in response to the moderator submitting the moderator-created dietary goal recommendation for the participant, transmitting, to the device associated with the digital avatar, the submitted moderator-created dietary goal recommendation as the dietary goal for the participant.

19. The computer program product of claim 17, further comprising:
retrieving a nutritional guideline provided for a population including at least one common characteristic with the participant;
retrieving a nutritional history of the participant;
comparing the retrieved nutritional guideline for the population including the at least one common characteristic with the participant with the retrieved nutritional history of the participant; and
in response to determining a nutritional gap in the retrieved nutritional history of the participant, generating an automatic dietary goal recommendation for the participant associated with the nutritional gap.

20. The computer program product of claim 17, wherein releasing the reward to the digital avatar, further comprises:
generating a digital content for the participant for sharing on a social media network, wherein the generated digital content is selected from the group consisting of a badge, an ornament, a status message, an enhancement for the digital avatar, and an evolutionary step for the digital avatar; and
providing a voucher for the participant for redeeming a third-party reward, wherein the redeemed third-party reward is selected from the group consisting of a discount, an amenity, and a material good from a third-party service.

\* \* \* \* \*